(12) United States Patent
Brunner

(10) Patent No.: US 11,833,324 B2
(45) Date of Patent: Dec. 5, 2023

(54) INTRAVENOUS CUFF ASSEMBLY

(71) Applicant: Sonia Brunner, Palm Bay, FL (US)

(72) Inventor: Sonia Brunner, Palm Bay, FL (US)

( * ) Notice: Subject to any disclaimer, the term of this patent is extended or adjusted under 35 U.S.C. 154(b) by 270 days.

(21) Appl. No.: 17/130,174

(22) Filed: Dec. 22, 2020

(65) Prior Publication Data

US 2022/0193335 A1     Jun. 23, 2022

(51) Int. Cl.
*A61M 5/158*     (2006.01)

(52) U.S. Cl.
CPC ..... *A61M 5/158* (2013.01); *A61M 2005/1586* (2013.01); *A61M 2210/083* (2013.01)

(58) Field of Classification Search
CPC .................. A61M 5/158; A61M 25/02; A61M 2005/1586; A61M 2210/083; A61M 2210/08; A61M 2210/086; A61M 2025/0253; A61M 2025/0206; A61M 2025/0246; A61M 2025/0213; A61M 2025/026; A61F 2013/00068; A61F 2013/00148; A61F 2013/00144
See application file for complete search history.

(56) References Cited

U.S. PATENT DOCUMENTS

| | | | |
|---|---|---|---|
| 3,726,280 A * | 4/1973 | Lacount | A61M 25/02 604/179 |
| 4,449,975 A | 5/1984 | Perry | |
| 4,470,410 A * | 9/1984 | Elliott | A61M 25/02 128/877 |
| 4,596,560 A * | 6/1986 | Simpson | A61M 25/02 604/174 |
| 5,188,608 A * | 2/1993 | Fritts | A61M 25/02 604/179 |
| 5,344,406 A * | 9/1994 | Spooner | D04B 21/12 604/179 |
| 5,643,216 A * | 7/1997 | White | A61M 25/02 604/174 |
| 5,897,519 A * | 4/1999 | Shesol | A61M 25/02 604/179 |
| 5,997,524 A * | 12/1999 | Burbank | A61M 5/158 604/502 |

(Continued)

FOREIGN PATENT DOCUMENTS

| | | | | |
|---|---|---|---|---|
| DE | 102020204630 A1 * | 10/2021 | ........... | A61F 13/022 |
| WO | WO-0115765 A1 * | 3/2001 | ............ | A61M 25/02 |

(Continued)

*Primary Examiner* — Katherine H Schwiker
*Assistant Examiner* — Adam J. Cermak

(57) ABSTRACT

An intravenous cuff assembly includes a cuff that is wearable around a user's arm to cover an injection site of an intravenous needle. The cuff is comprised of a resiliently stretchable material to compress against the intravenous needle thereby inhibiting movement of the intravenous needle. A plurality of first mating members and a plurality of second mating members is each coupled to the cuff. Each of the second mating members is releasably matable to a respective one of the first mating members for adjusting dimensions of the cuff. A plurality of third mating members and a plurality of fourth mating members is each coupled to the cuff. Each of the fourth mating members is releasably matable to a respective one of the third mating members for adjusting dimensions of the cuff.

5 Claims, 4 Drawing Sheets

(56) References Cited

U.S. PATENT DOCUMENTS

| | | | | |
|---|---|---|---|---|
| 6,276,364 B1* | 8/2001 | Warner | A61M 25/02 128/846 |
| 7,022,111 B2 | 4/2006 | Duplessie | |
| 8,597,254 B1* | 12/2013 | Mullet | A61M 5/1418 604/179 |
| 8,690,835 B1* | 4/2014 | Parris | A41D 13/1236 604/179 |
| D785,188 S | 4/2017 | Cilone | |
| 11,090,184 B1* | 8/2021 | Prody | A61M 25/02 |
| 11,202,477 B1* | 12/2021 | Dawson | A41D 31/02 |
| 11,389,623 B1* | 7/2022 | Shoemaker, Jr. | A61B 46/27 |
| 2007/0083163 A1* | 4/2007 | Rydell | A61M 25/02 604/179 |
| 2007/0276331 A1* | 11/2007 | Campbell | A61M 25/02 604/174 |
| 2010/0137805 A1* | 6/2010 | Farchione | A61M 25/02 604/179 |
| 2011/0230863 A1* | 9/2011 | Lentini | A61M 25/02 604/541 |
| 2011/0301544 A1* | 12/2011 | Dixon | A61M 25/02 604/179 |
| 2013/0012883 A1* | 1/2013 | Fitzgerald | A61M 39/08 604/179 |
| 2014/0060547 A1* | 3/2014 | Vallino | A61F 5/05858 128/845 |
| 2014/0081211 A1* | 3/2014 | Laird | A61M 25/02 604/179 |
| 2014/0350474 A1* | 11/2014 | Andreae | A61M 25/02 604/179 |
| 2015/0038927 A1* | 2/2015 | Prody | A61M 25/02 604/327 |
| 2015/0283358 A1* | 10/2015 | Bouchard | A61M 25/02 604/179 |
| 2016/0015939 A1* | 1/2016 | Rawls | A61M 25/02 604/510 |
| 2016/0302954 A1* | 10/2016 | Mirabella | A61F 5/0585 |
| 2018/0221213 A1* | 8/2018 | Hitschmann | A61F 13/085 |
| 2018/0330638 A1* | 11/2018 | Fridman | G09F 3/005 |
| 2019/0046772 A1* | 2/2019 | Jutras | A61M 25/02 |
| 2019/0134353 A1* | 5/2019 | Fitzgerald | A61F 13/143 |
| 2020/0029634 A1* | 1/2020 | Wilson | A41D 19/0034 |
| 2020/0129737 A1* | 4/2020 | Woodard | A61M 25/02 |
| 2021/0052025 A1* | 2/2021 | Colon-Alfonso | A41D 27/10 |
| 2021/0212394 A1* | 7/2021 | Wu | A41D 13/1245 |
| 2021/0346651 A1* | 11/2021 | Lerner | A61M 1/3633 |
| 2021/0386939 A1* | 12/2021 | Spataro | A61M 5/427 |
| 2022/0161001 A1* | 5/2022 | Levy | A61M 25/02 |
| 2022/0168495 A1* | 6/2022 | Locke | A61M 1/962 |
| 2022/0233837 A1* | 7/2022 | Hommes | A61L 31/16 |
| 2022/0257907 A1* | 8/2022 | Queen | A61M 25/02 |

FOREIGN PATENT DOCUMENTS

| | | | | |
|---|---|---|---|---|
| WO | WO2014043718 | | 3/2014 | |
| WO | WO-2014197572 A1 | * | 12/2014 | A61F 13/022 |

* cited by examiner

INTRAVENOUS CUFF ASSEMBLY

(b) CROSS-REFERENCE TO RELATED APPLICATIONS

Not Applicable

(c) STATEMENT REGARDING FEDERALLY SPONSORED RESEARCH OR DEVELOPMENT

Not Applicable

(d) THE NAMES OF THE PARTIES TO A JOINT RESEARCH AGREEMENT

Not Applicable

(e) INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

(f) STATEMENT REGARDING PRIOR DISCLOSURES BY THE INVENTOR OR JOINT INVENTOR

Not Applicable

(g) BACKGROUND OF THE INVENTION

(1) Field of the Invention

The disclosure relates to cuff devices and more particularly pertains to a new cuff device for inhibiting malfunction of an intravenous needle and associated tubing. The device includes a plurality of mating members for adjusting the size of the cuff to accommodate a variety of users.

(2) Description of Related Art Including Information Disclosed Under 37 CFR 1.97 and 1.98

The prior art relates to cuff devices including a variety of straps and sleeves that are positionable around a user's arm to restrain an intravenous needle. In each case the cuff devices are releasably attached to themselves to form a closed loop. The prior art discloses a unitary sleeve that is wearable over a user's arm to cover an injection site and which is comprise of a fluid impermeable material.

(h) BRIEF SUMMARY OF THE INVENTION

An embodiment of the disclosure meets the needs presented above by generally comprising a cuff that is wearable around a user's arm to cover an injection site of an intravenous needle. The cuff is comprised of a resiliently stretchable material to compress against the intravenous needle thereby inhibiting movement of the intravenous needle. A plurality of first mating members and a plurality of second mating members is each coupled to the cuff. Each of the second mating members is releasably matable to a respective one of the first mating members for adjusting dimensions of the cuff. A plurality of third mating members and a plurality of fourth mating members is each coupled to the cuff. Each of the fourth mating members is releasably matable to a respective one of the third mating members for adjusting dimensions of the cuff.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

(i) BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

(j) DETAILED DESCRIPTION OF THE INVENTION

Figure 1:
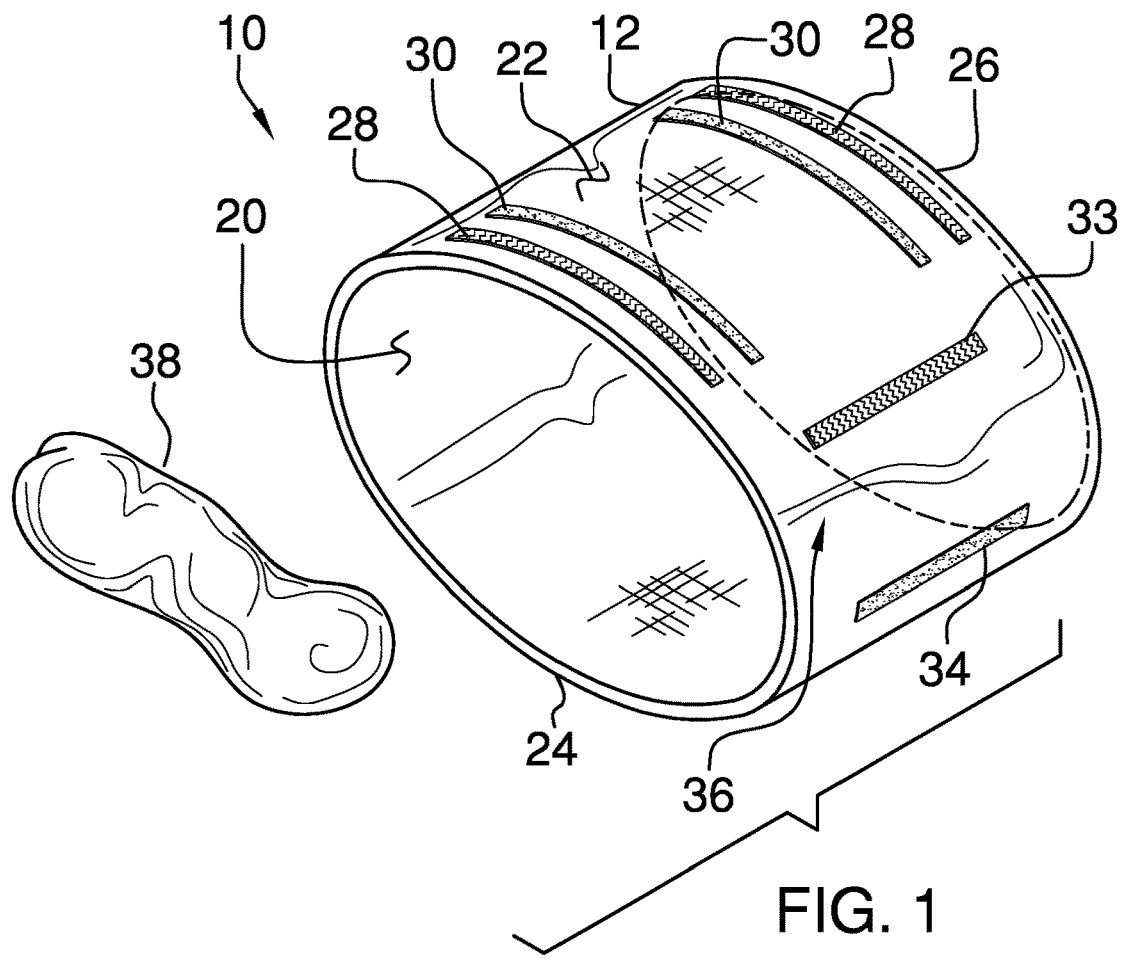
FIG. 1 is a perspective view of an intravenous cuff assembly according to an embodiment of the disclosure.
Figure 2:
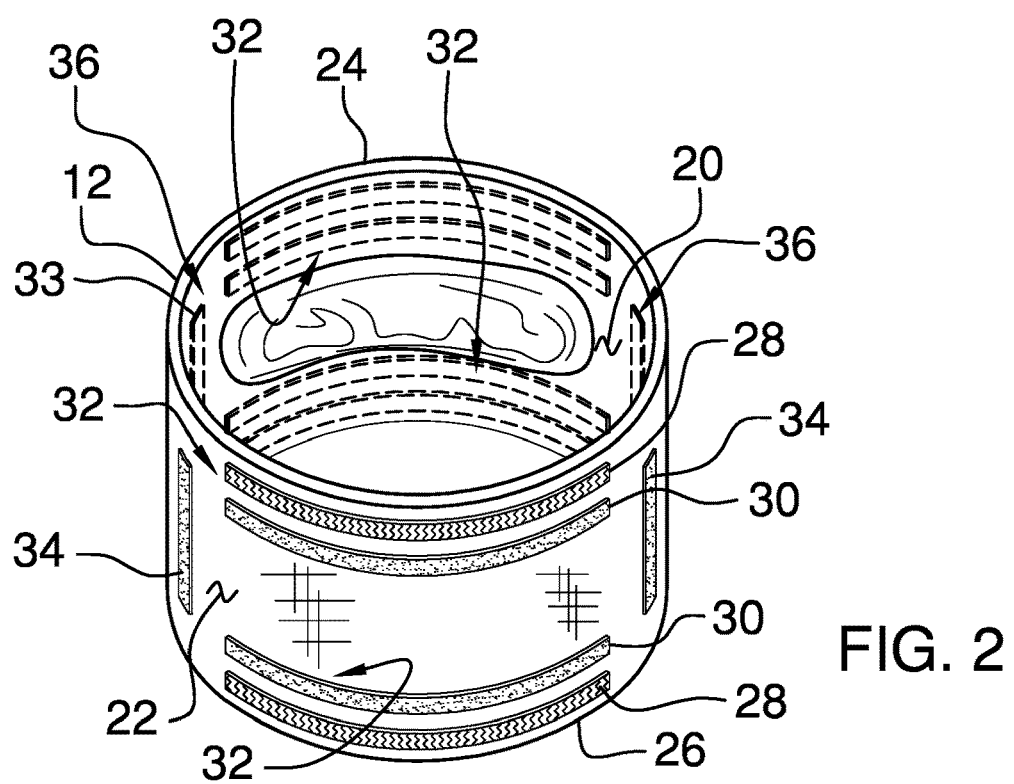
FIG. 2 is a perspective phantom view of a cuff of an embodiment of the disclosure.
Figure 3:
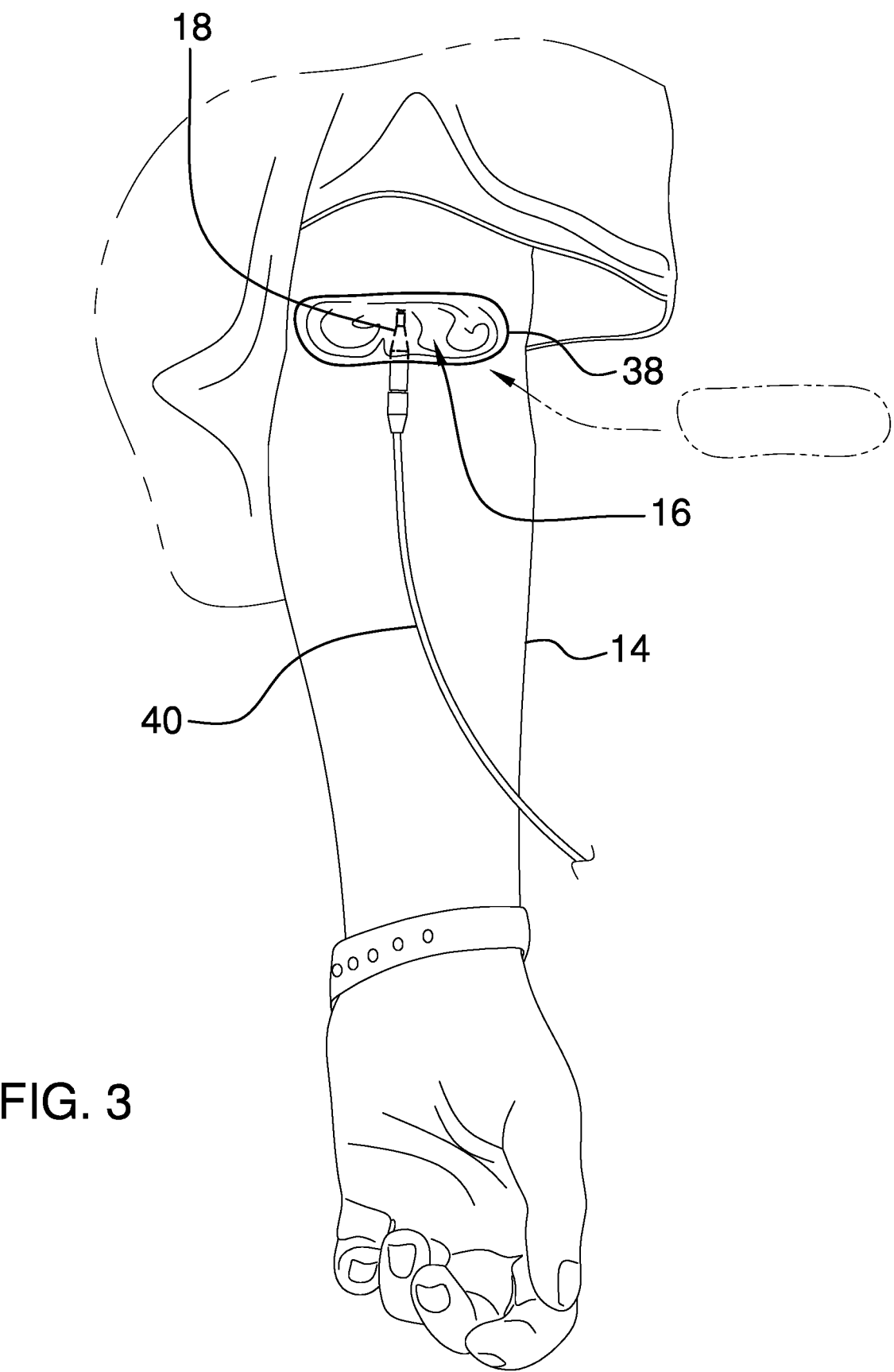
FIG. 3 is a perspective in-use view of an embodiment of the disclosure showing a pad being positioned over an injection site.
Figure 4:
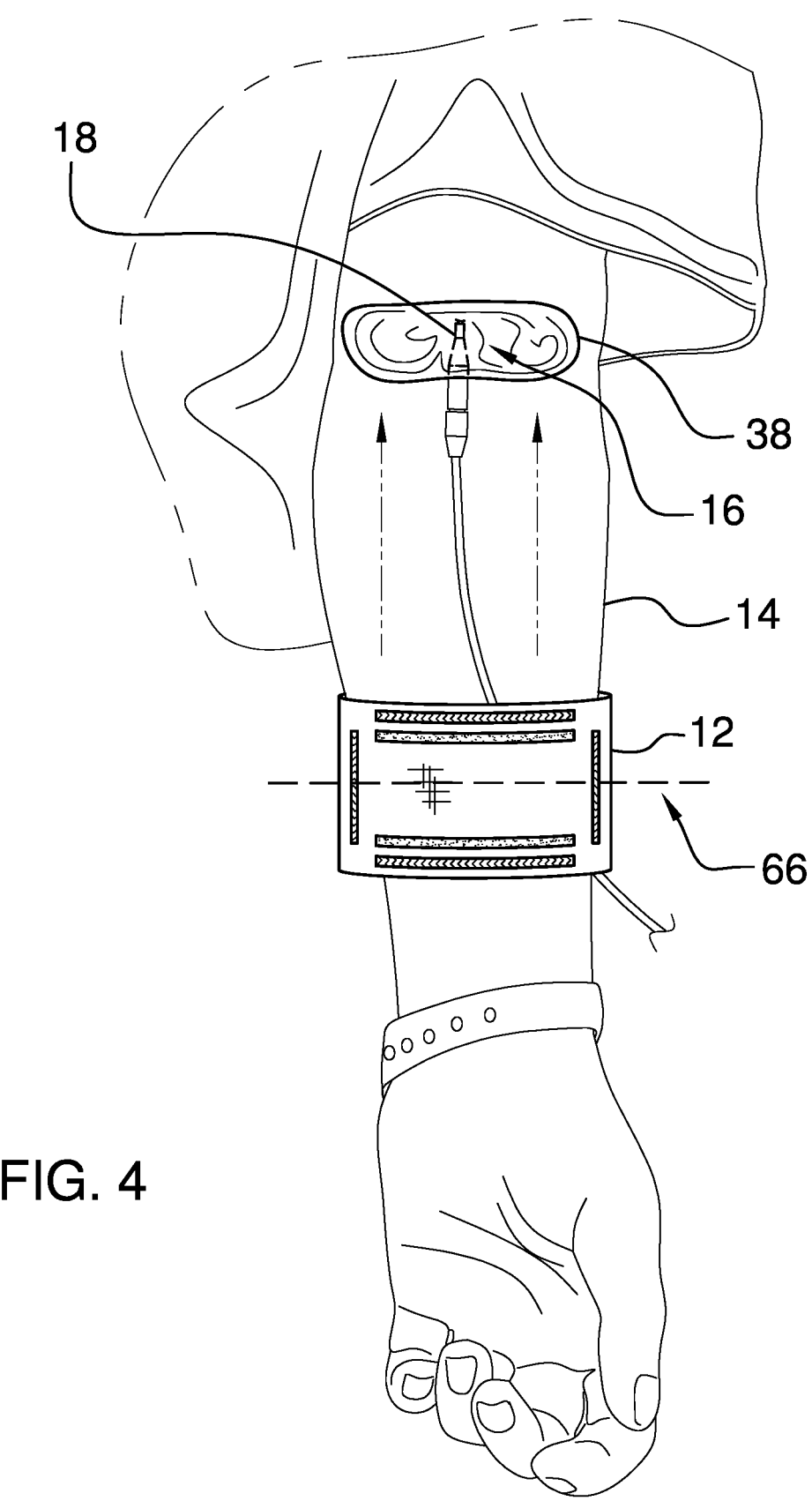
FIG. 4 is a perspective in-use view of an embodiment of the disclosure showing a cuff being slid into position to cover an injection site.
Figure 5:
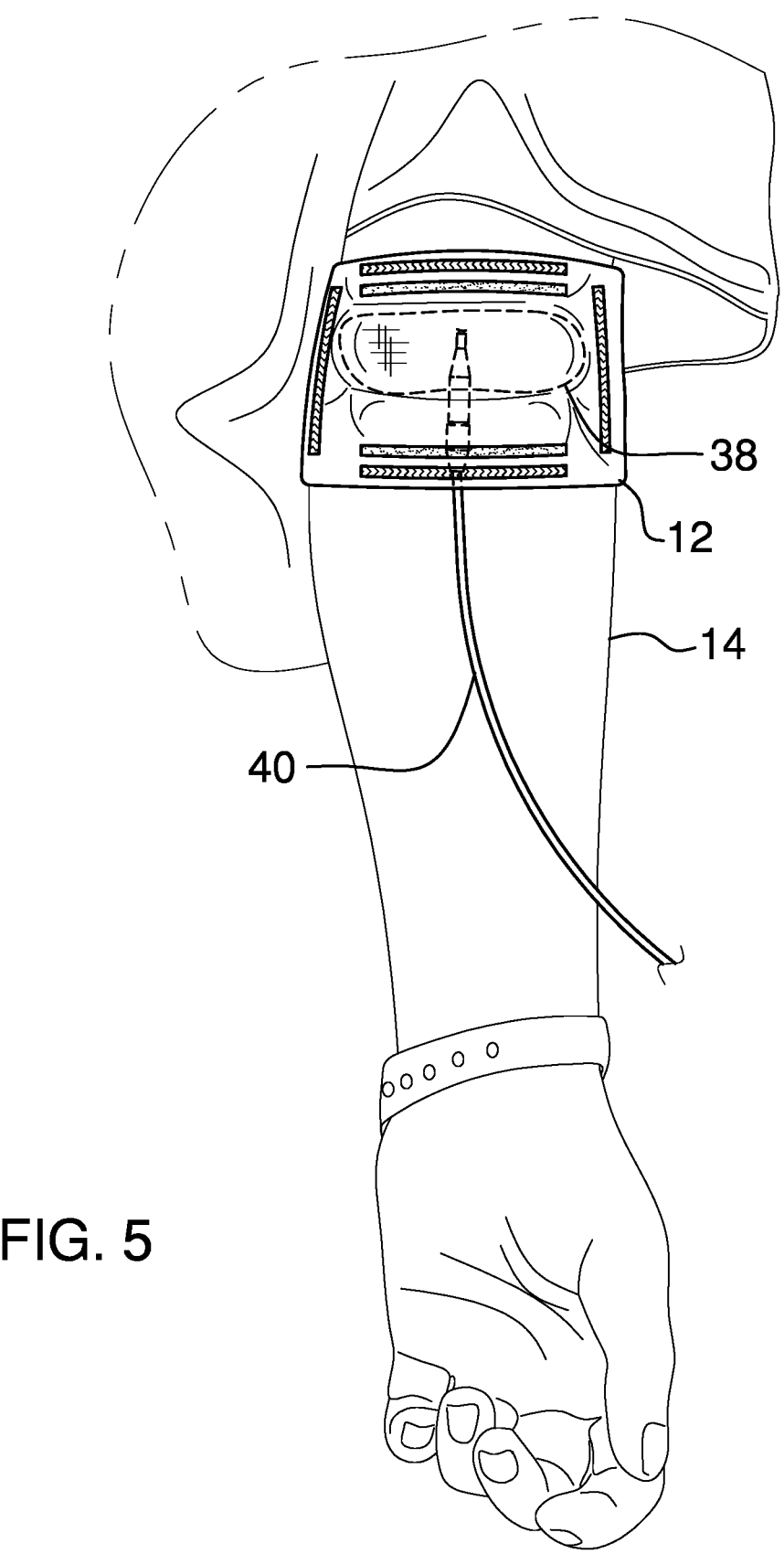
FIG. 5 is a phantom in-use view of an embodiment of the disclosure.

With reference now to the drawings, and in particular to FIGS. 1 through 5 thereof, a new cuff device embodying the principles and concepts of an embodiment of the disclosure and generally designated by the reference numeral 10 will be described.

As best illustrated in FIGS. 1 through 5, the intravenous cuff assembly 10 generally comprises a cuff 12 that is wearable around a user's arm 14 to cover an injection site 16 of an intravenous needle 18. The cuff 12 is comprised of a resiliently stretchable material to compress against the intravenous needle 18 thereby inhibiting movement of the intravenous needle 18. The cuff 12 has an inside surface 20, an outside surface 22, a front edge 24 and a back edge 26. A plurality of first mating members 28 is each coupled to the cuff 12 and each of the first mating members 28 is positioned on the outside surface 22 of the cuff 12. The first mating members 28 are spaced apart from each other and are distributed around the cuff 12. Moreover, each of the first mating members 28 is distributed along a respective one of the front edge 24 and the back edge 26 of the cuff 12.

A plurality of second mating members 30 is each coupled to the cuff 12 and each of the second mating members 30 is strategically positioned with respect to the plurality of first mating members 28. Each of the second mating members 30 is releasably matable to a respective one of the first mating members 28 for adjusting dimensions of the cuff 12 to accommodate a variety of sizes of user's arms 14. Each of the second mating members 30 is positioned on the outside surface 22 of the cuff 12 and each of the second mating members 30 is aligned with a respective one of the first mating members 28. Additionally, each of the second mating members 30 is positioned between the respective first mating member 28 and a centerline of the cuff 12. Each of the first mating members 28 and each of the second mating members 30 may comprise complementary portions of a hook and loop fastener, a complementary mechanical fasteners or any other means of multiple use, releasable coupling. As is most clearly shown in FIG. 2, the first mating members 28 and the second mating members 30 are arranged into a pair of groups 32, and each of the groups 32 are positioned on opposite sides of the cuff 12 from each other.

A plurality of third mating members 33 is each coupled to the cuff 12 and each of the third mating members 33 is positioned on the outside surface 22 of the cuff 12. Each of the third mating members 33 extends substantially between the front edge 24 and the back edge 26 of the cuff 12. Additionally, the third mating members 33 are spaced apart from each other and are distributed around the cuff 12. A plurality of fourth mating members 34 is each coupled to the cuff 12 and each of the fourth mating members 34 is strategically positioned with respect to the third mating members 33. Each of the fourth mating members 34 is releasably matable to a respective one of the third mating members 33 for adjusting dimensions of the cuff 12. In this way the cuff 12 can accommodate a variety of sizes of user's arms 14.

Each of the fourth mating members 34 is positioned on the outside surface 22 of the cuff 12 and each of the fourth mating members 34 extends substantially between the front edge 24 and the back edge 26 of the cuff 12. The fourth mating members 34 are spaced apart from each other and are distributed around the cuff 12, and each of the fourth mating members 34 is spaced from the respective third mating member 32. Each of the third mating members 33 and the fourth mating members 34 may comprise complementary portions of a hook and loop fastener or other type of multiple use, releasable fastener. Additionally, as is most clearly shown in FIG. 2, the third mating members 33 and the fourth mating members 34 may be arranged into a pair of groups 36 that is each positioned between respective groups 32 of the first mating members 28 and second mating members 30.

A pad 38 is provided and the pad 38 is positionable between the cuff 12 and the injection site 16. The pad 38 is comprised of a fluid absorbent material to absorb fluids that leak from the injection site 16. The inside surface 20 of the cuff 12 compresses the pad 38 against the user's arm 14 when the cuff 12 and the pad 38 are worn. The pad 38 may be provided in sterile packaging thereby facilitating the pad 38 to be safely placed over the intravenous needle 18. The fluid absorbent material may be cotton, a fluid absorbing gel or any other material that is soft to the touch and which can absorb bodily fluids.

In use, the pad 38 is positioned over the injection site 16 and the cuff 12 is slipped over the user's arm 14 until the cuff 12 covers the injection site 16. In this way the pad 38 is retained in place to absorb bodily fluids and the cuff 12 restrains the intravenous needle 18 and associated tubing 40. Thus, the user can move their arm 14 without the fear of dislodging the intravenous needle 18 or kinking the associated tubing 40. In this way a monitoring device, such as is commonly employed in a hospital setting, will not begin emitting a warning beep that is caused by a malfunction in the intravenous needle 18. Thus, caregivers in the hospital setting do not waste time attending to false alarm 14s with respect to kinked tubing or dislodging of intravenous needles that result from normal movement of the user.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An intravenous cuff assembly for stabilizing an intravenous needle in an injection site, said assembly comprising:

a cuff being wearable around a user's arm wherein said cuff is configured to cover an injection site of an intravenous needle, said cuff being comprised of a resiliently stretchable material wherein said cuff is configured to compress against the intravenous needle thereby inhibiting movement of the intravenous needle, said cuff having an inside surface, an outside surface, a front edge and a back edge;

a plurality of first mating members, each of said first mating members being coupled to said cuff;

a plurality of second mating members, each of said second mating members being coupled to said cuff, each of said second mating members being releasably matable to a respective one of said first mating members for adjusting dimensions of said cuff wherein said cuff is configured to accommodate a variety of sizes of user's arms;

a plurality of third mating members, each of said third mating members being coupled to said cuff;

a plurality of fourth mating members, each of said fourth mating members being coupled to said cuff, each of said fourth mating members being releasably matable to a respective one of said third mating members for adjusting dimensions of said cuff wherein said cuff is configured to accommodate a variety of sizes of user's arms, each of said fourth mating members being positioned on said outside surface of said cuff;

a pad, said pad being elongated, said pad being positionable between said cuff and the injection site having a central longitudinal axis of said pad extending along a centerline of said cuff wherein said pad is positioned extending parallel to and between two of said second mating members, said pad being comprised of a fluid absorbent material wherein said pad is configured to absorb fluids that leak from the injection site;

wherein each of said first mating members is positioned on said outside surface of said cuff, said first mating members being spaced apart from each other and being distributed around said cuff, each of said first mating members being distributed along a respective one of said front edge and said back edge of said cuff; and wherein each of said second mating members is positioned on said outside surface of said cuff, each of said second mating members being aligned with a respective one of said first mating members, each of said second mating members being positioned between said respective first mating member and the centerline of said cuff.

2. The assembly according to claim 1, wherein:

said cuff has an inside surface, an outside surface, a front edge and a back edge; and each of said third mating members is positioned on said outside surface of said cuff, each of said third mating members extending substantially between said front edge and said back edge of said cuff, said third mating members being spaced apart from each other and being distributed around said cuff.

3. The assembly according to claim 2, wherein each of said fourth mating members extends substantially between said front edge and said back edge of said cuff, said fourth mating members being spaced apart from each other and being distributed around said cuff, each of said fourth mating members being spaced from said respective third mating member.

4. The assembly according to claim 1, wherein:

said cuff has an inside surface, an outside surface, a front edge and a back edge; and said inside surface of said cuff compressing said pad against the user's arm when said cuff and said pad are worn.

5. An intravenous cuff assembly for stabilizing an intravenous needle in an injection site, said assembly comprising:

a cuff being wearable around a user's arm wherein said cuff is configured to cover an injection site of an intravenous needle, said cuff being comprised of a resiliently stretchable material wherein said cuff is configured to compress against the intravenous needle thereby inhibiting movement of the intravenous needle, said cuff having an inside surface, an outside surface, a front edge and a back edge;

a plurality of first mating members, each of said first mating members being coupled to said cuff, each of said first mating members being positioned on said outside surface of said cuff, said first mating members being spaced apart from each other and being distributed around said cuff, each of said first mating members being distributed along a respective one of said front edge and said back edge of said cuff;

a plurality of second mating members, each of said second mating members being coupled to said cuff, each of said second mating members being releasably matable to a respective one of said first mating members for adjusting dimensions of said cuff wherein said cuff is configured to accommodate a variety of sizes of user's arms, each of said second mating members being positioned on said outside surface of said cuff, each of said second mating members being aligned with a respective one of said first mating members, each of said second mating members being positioned between said respective first mating member and a centerline of said cuff;

a plurality of third mating members, each of said third mating members being coupled to said cuff, each of said third mating members being positioned on said outside surface of said cuff, each of said third mating members extending substantially between said front edge and said back edge of said cuff, said third mating members being spaced apart from each other and being distributed around said cuff;

a plurality of fourth mating members, each of said fourth mating members being coupled to said cuff, each of said fourth mating members being releasably ma table to a respective one of said third mating members for adjusting dimensions of said cuff wherein said cuff is configured to accommodate a variety of sizes of user's arms, each of said fourth mating members being positioned on said outside surface of said cuff, each of said fourth mating members extending substantially between said front edge and said back edge of said cuff, said fourth mating members being spaced apart from each other and being distributed around said cuff, each of said fourth mating members being spaced from said respective third mating member; and a pad, said pad being elongated, said pad being positionable between said cuff and the injection site having a central longitudinal axis of said pad extending along the centerline of said cuff wherein said pad is positioned extending parallel to and between two of said second mating members, said pad being comprised of a fluid absorbent material wherein said pad is configured to absorb fluids that leak from the injection site, said inside surface of said cuff compressing said pad against the user's arm when said cuff and said pad are worn.

* * * * *